(12) United States Patent
Chen et al.

(10) Patent No.: US 10,638,971 B2
(45) Date of Patent: May 5, 2020

(54) METHODS AND APPLICATIONS FOR DETECTION OF BREATH FLOW AND THE SYSTEM THEREOF

(71) Applicant: Somnics, Inc., San Jose, CA (US)

(72) Inventors: Chung-Chu Chen, Zhubei (TW); Chen-Ning Huang, Zhubei (TW)

(73) Assignee: Somnics, Inc. (USA), San Jose, CA (US)

(*) Notice: Subject to any disclaimer, the term of this patent is extended or adjusted under 35 U.S.C. 154(b) by 742 days.

(21) Appl. No.: 15/121,684

(22) PCT Filed: Feb. 25, 2015

(86) PCT No.: PCT/US2015/017404
§ 371 (c)(1),
(2) Date: Aug. 25, 2016

(87) PCT Pub. No.: WO2015/130717
PCT Pub. Date: Sep. 3, 2015

(65) Prior Publication Data
US 2016/0361012 A1    Dec. 15, 2016

Related U.S. Application Data

(60) Provisional application No. 61/944,107, filed on Feb. 25, 2014.

(51) Int. Cl.
*A61B 5/087*    (2006.01)
*A61B 1/267*    (2006.01)
(Continued)

(52) U.S. Cl.
CPC ............ *A61B 5/4818* (2013.01); *A61B 1/267* (2013.01); *A61B 5/087* (2013.01); *A61B 5/4833* (2013.01);
(Continued)

(58) Field of Classification Search
CPC ....... A61B 5/4818; A61B 1/267; A61B 5/087; A61B 5/7203; A61B 5/7225; A61H 9/0057
(Continued)

(56) References Cited

U.S. PATENT DOCUMENTS 2,937,445 A    5/1960 Erickson
5,456,264 A *  10/1995 Series .................... A61B 5/083
                                                       600/533
(Continued)

FOREIGN PATENT DOCUMENTS

WO    2013152403 A1    10/2013
WO    2013177338 A1    11/2013

OTHER PUBLICATIONS

Jager et al., Flouroscopic MR of teh Pharynx in Patients with Obstructive Sleep Apnea, AJNR AM J. Neuroradiol 19: 1205?1214, Aug. 1998 [retreived on May 12, 2015 from the internet <URL http//www.ajnr.org/content/19/7/1205. full.pdf> p. 1205 and 1206.
(Continued)

*Primary Examiner* — Navin Natnithithadha
(74) *Attorney, Agent, or Firm* — Stinson LLP

(57) ABSTRACT

The present invention provides methods for characterizing obstructive sleep apnea (OSA) patients in the treatment of OSA, and devices thereof. The methods comprise measuring polysomnography of said patients; analyzing polysomnography, and determining a characteristic of the polysomnography and selections of suitable treatments based on the patterns.

24 Claims, 16 Drawing Sheets

(51) Int. Cl.
*A61B 5/00* (2006.01)
*A61H 9/00* (2006.01)

(52) U.S. Cl.
CPC .......... *A61B 5/7203* (2013.01); *A61B 5/7225* (2013.01); *A61H 9/0057* (2013.01); *A61B 2562/0247* (2013.01)

(58) Field of Classification Search
USPC ........................................ 600/538, 532, 529
See application file for complete search history.

(56) References Cited

U.S. PATENT DOCUMENTS

| | | |
|---|---|---|
| 5,692,523 A | 12/1997 | Croll et al. |
| 5,876,199 A | 3/1999 | Bergersen |
| 2003/0208149 A1 | 11/2003 | Coffey |
| 2005/0027207 A1 | 2/2005 | Westbrook et al. |
| 2005/0131283 A1 | 6/2005 | Grant et al. |
| 2005/0217678 A1 | 10/2005 | McCormick et al. |
| 2007/0021795 A1 | 1/2007 | Tehrani |
| 2009/0120446 A1 | 5/2009 | Vaska et al. |
| 2011/0217719 A1 | 9/2011 | Gozal et al. |
| 2011/0220124 A1 | 9/2011 | Vaska et al. |
| 2012/0108945 A1 | 5/2012 | Ni |
| 2014/0034064 A1 | 2/2014 | Chen et al. |

OTHER PUBLICATIONS

International Search Report and Written Opinion for Application PCT/US2015/17404, dated Jun. 12, 2015, 18 pages.

* cited by examiner

Type I
Posteroanterior Collapse

Type II
Lateral Collapse

Type III
Annular Collapse

Type I video

Type II video

Type III video

Flow limitation detector

Flow limitation detector
with Negative pressure therapy

METHODS AND APPLICATIONS FOR DETECTION OF BREATH FLOW AND THE SYSTEM THEREOF

BACKGROUND OF THE INVENTION

Polysomnography (PSG) is a comprehensive recording of the biophysiological changes that occur during sleep. The PSG may monitor many body functions including brain (EEG), eye movements (EOG), muscle activity or skeletal muscle activation (EMG) and heart rhythm (ECG) during sleep. After the identification of the sleep disorder/sleep apnea in the 1970s, the breathing functions respiratory airflow and respiratory effort indicators were added along with peripheral pulse oximetry.

For example, nasal and oral airflow can be measured using pressure transducers, and/or a thermocouple, fitted in or near the nostrils; the pressure transducer is considered the more sensitive. This allows the clinician/researcher to measure the rate of respiration and identify interruptions in breathing.

SUMMARY OF THE INVENTION

In one aspect provides herein methods for characterizing obstructive sleep apnea (OSA) patients in the treatment of OSA comprising measuring polysomnography of said patients; analyzing polysomnography, and determining a characteristic of the polysomnography. In some embodiments, the measuring polysomnography is to measure inspiratory and expiratory air flows. In some embodiments, the analyzing polysomnography is to analyze inspiratory and expiratory flow limitations.

In another aspect provides herein methods of selecting obstructive sleep apnea (OSA) patient for a suitable OSA treatment comprising measuring polysomnography of said patients; analyzing the polysomnography and determining a type of said OSA patient. In some embodiments, the analyzing polysomnography is to analyze inspiratory and expiratory flow limitations. In some embodiments, the determining a type of said OSA patient is based on the type of inspiratory and expiratory flow limitations.

In further aspect provides herein systems of characterizing obstructive sleep apnea (OSA) patients in the treatment of OSA comprising a sensor unit, for detecting polysomnography of an OSA patient and generating a flow limitation signal; a signal conditioning unit, coupled to the sensor unit, for amplifying the flow limitation signal and filtering out unwanted noises; a data acquisition unit, for converting the flow limitation signal to a digital data; a processor unit, for operating the digital data to generate flow limitation indexes; a storage unit for saving the digital data and the flow limitation indexes; and a communication interface unit, for communicating with users and external devices.

In another aspect provides herein systems of selecting OSA patient for a suitable OSA treatment comprising a sensor unit, for detecting polysomnography of an OSA patient and generating a flow limitation signal; a signal conditioning unit, coupled to the sensor unit, for amplifying the flow limitation signal and filtering out unwanted noises; a data acquisition unit, for converting the flow limitation signal to a digital data; a processor unit, for operating the digital data to generate flow limitation indexes; a storage unit for saving the digital data and the flow limitation indexes; and a communication interface unit, for communicating with users and external devices.

In still another aspect provides herein systems of characterizing obstructive sleep apnea (OSA) patients in the treatment of OSA or selecting OSA patient for a suitable OSA treatment combined with negative pressure therapy. In some embodiments the systems comprising: a sensor unit; a signal conditioning unit; a data acquisition unit; a processor unit; a storage unit; a communication interface unit; and further comprising: a negative pressure source, for providing a negative pressure to an OSA patient; a tube with two terminals, one terminal connecting the negative pressure source and the other terminal placed in the OSA patient's oral cavity deviling a negative pressure from the negative pressure source to the OSA patient's oral cavity; an oral interface formed on the terminal placed in the OSA patient's cavity, for maintaining sealing of the OSA patient's oral cavity while the negative pressure is being delivered; a saliva container connected to the tubing, for collecting saliva secreted from the OSA patient's oral.

In another aspect provides methods for characterizing obstructive sleep apnea (OSA) patients for use in the treatment of OSA comprising taking images of upper airway endoscopic imaging with Muller maneuver, analyzing said images, and characterizing said OSA patients based on a characteristic of the images.

In another aspect provides methods selecting OSA patient for a suitable OSA treatment comprising taking images of upper airway endoscopic imaging with Muller maneuver; analyzing said images; and selecting the suitable OSA treatment based on a characteristic of the images.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
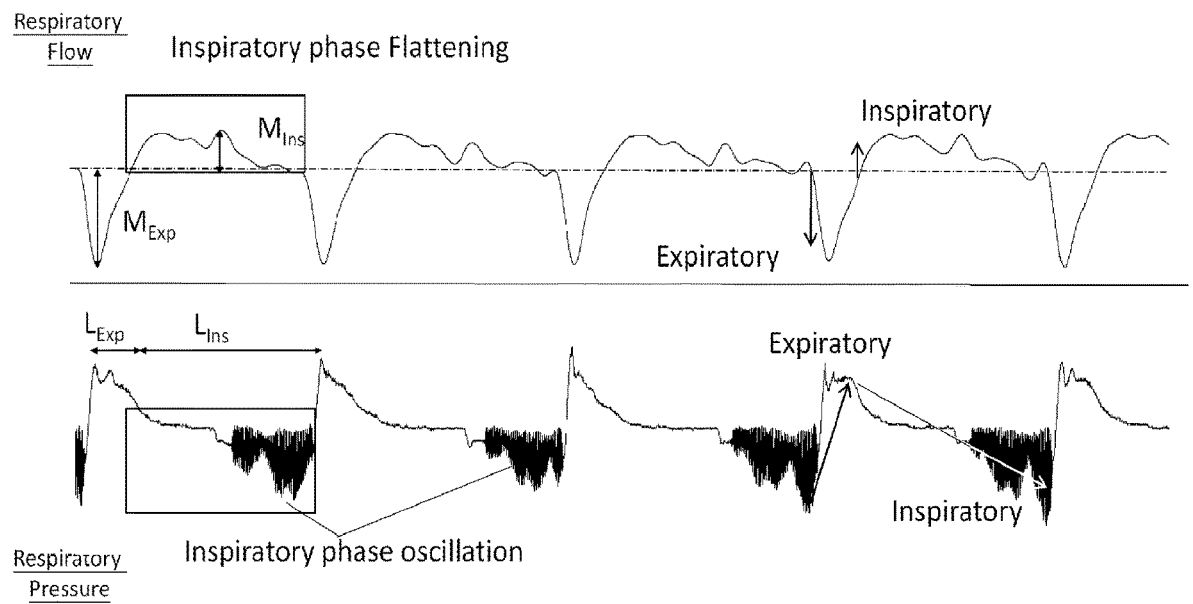
FIG. 1 shows the particularly selected characteristics of inspiratory flow limitation in waveforms related to breath magnitude, breath length, and phase oscillation.

Oral and external devices for treating sleep apnea and snoring have been disclosed in several publications utilizing several theories. With these possible treatments, it is important to determine which method or device to treat sleep apnea and snoring. There are a few publications providing possible diagnostic methods focusing on detection of either high upper airway resistance and/or inspiratory flow limitations. Inspiratory flow limitation during sleep is defined by a decreasing intrathoracic pressure without a corresponding increase in airway flow rate. This alinearity in the pressure/flow relationship during inspiration is commonly caused by narrowing of a hypotonic upper airway in response to the negative intrathoracic pressure developed during inspiration. The publications related to the detection of inspiratory flow limitation mainly focus on the detection of inspiratory flow limitations, or a peak inspiration of an airflow wave corresponding to the breathing of a patient. However none of them provide a solution on characterizing obstructive sleep apnea (OSA) patients correlating to selections of proper treatments for different type of OSA patients.

In some embodiments, there are provided methods for characterizing obstructive sleep apnea (OSA) patients in the treatment of OSA based on the selected characteristics of flow limitations, and diagnostic devices or systems thereof. In some embodiments provide methods of selecting obstructive sleep apnea (OSA) patient for a suitable OSA treatment based on the different characters of flow limitations in OSA patients, and diagnostic devices and systems thereof.

In some embodiments provide herein a method for characterizing obstructive sleep apnea (OSA) patients in the treatment of OSA comprising measuring polysomnography of said patients; analyzing polysomnography, and determining a characteristic of the polysomnography. In some embodiments, the measuring polysomnography is to measure inspiratory and expiratory air flows. In some embodiments, the analyzing polysomnography is to analyze inspiratory and expiratory flow limitations. In some embodiments, the analyzing inspiratory and expiratory flow limitations is to analyze inspiratory and expiratory flow magnitude changes (i.e., $M_{Ins}$, and $M_{Exp}$). In some embodiments, the analyzing inspiratory and expiratory flow limitation is to analyze inspiratory and expiratory flow period length (i.e., $L_{Ins}$, and $L_{Exp}$) changes. In some embodiments, the analyzing inspiratory and expiratory flow limitation is to analyze inspiratory phase attenuation and expiratory phase attenuation. In some embodiments, the analyzing inspiratory and expiratory flow limitation is to analyze inspiratory and expiratory slope changes. In some embodiments, the analyzing inspiratory and expiratory flow limitation is to analyze inspiratory and expiratory phase oscillations.

In some embodiments, the characteristic of the polysomnography is determined by one or more flow limitation indexes selected in a group consisting of Inspiratory flow limitation percentage (IFL);

Expiratory flow limitation percentage (EFL); and

Mix flow limitation percentage (MFL);

wherein, the inspiratory flow limitation percentage is the number of inspiratory flow limitation event/the number of total breath cycle;

the expiratory flow limitation percentage is the number of expiratory flow limitation event/the number of total breath cycle;

the mix flow limitation percentage is the number of mix flow limitation event/the number of total breath cycle. In certain embodiments, the characteristic of the polysomnography determined as an inspiratory flow limitation group when the IFL>20% and IFL>EFL. In certain embodiments, the characteristic of the polysomnography determined as an expiratory flow limitation group when the EFL>0.75% and EFL>IFL. In certain embodiments, the characteristic of the polysomnography determined as a mix flow limitation group when the MFL>1%. In certain embodiments, the characteristic of the polysomnography determined as a not classified group when the characteristic determined does not meet the flow limitation indexes.

In another embodiment provides herein a method of selecting obstructive sleep apnea (OSA) patient for a suitable OSA treatment comprising measuring polysomnography of said patients; analyzing the polysomnography and determining a type of said OSA patient. In some embodiments, the analyzing polysomnography is to analyze inspiratory and expiratory flow limitations. In some embodiments, the determining a type of said OSA patient is based on the type of inspiratory and expiratory flow limitations. In some embodiments, the type of said OSA patient determined by a flow limitation index selected from a group consisting of Inspiratory flow limitation percentage (IFL);

Expiratory flow limitation percentage (EFL); and

Mix flow limitation percentage (MFL);

wherein, the inspiratory flow limitation percentage is the number of inspiratory flow limitation event/the number of total breath cycle;

the expiratory flow limitation percentage is the number of expiratory flow limitation event/the number of total breath cycle;

the mix flow limitation percentage is the number of mix flow limitation event/the number of total breath cycle. In certain embodiments, the flow limitation index is the expiratory flow limitation percentage. In certain embodiments, the type of said OSA patient determined as suitable for an oral negative therapy when the flow limitation index is less a threshold of 2%.

The invention methods or devices for characterizing obstructive sleep apnea (OSA) patients in the treatment of OSA are based on a clinical study conducted to select suitable patients for oral pressure therapy. There are available in the art standardized procedures for detecting flow limitation based on analysis of the pressure-flow aspect of the respiration cycle. The collection of inspiratory flow limitation waveforms of OSA patents were measured and the respiratory flow and/or respiratory pressure were typically analyzed, and the key characteristics of inspiration flow limitations were determined. Based on the determined characteristics, a suitable OSA treatment was applied to patients who got a better treatment.

In further embodiment provides herein a system for detecting flow limitation of obstructive sleep apnea (OSA) patients comprising: a sensor unit, for detecting polysomnography of an OSA patient and generating a flow limitation signal; a signal conditioning unit, coupled to the sensor unit, for amplifying the flow limitation signal and filter out unwanted noises; a data acquisition unit, for converting the flow limitation signal to a digital data; a processor unit, for operating the digital data to generate a flow limitation indexes; a storage unit for saving the digital data and the flow limitation indexes; and a communication interface unit, for communicating with users and external devices.

In another embodiment provides herein a system for detecting flow limitation of an obstructive sleep apnea (OSA) patient comprising: a sensor unit; a signal conditioning unit; a data acquisition unit; a processor unit; a storage unit; a communication interface unit; and further comprising: a negative pressure source, for providing a negative pressure to an OSA patient; a tube with two terminals, one of its terminal connecting the negative pressure source and the other terminal placed in the OSA patient's oral cavity, deviling a negative pressure from the negative pressure source to the OSA patient's oral cavity; an oral interface formed on the terminal placed in the OSA patient's cavity, for maintaining sealing of the OSA patient's oral cavity while the negative pressure is being delivered; a saliva container connected to the tube, for collecting saliva secreted from the OSA patient's oral cavity; and a console, for operating the negative pressure based on the flow limitation indexes; a positioner, to place the sensor on the oral interface.

FIG. 1 shows certain particularly selected characteristics of inspiratory flow limitation in waveforms. Based on the exemplary waveforms, the particularly selected characteristics of inspiration flow limitation comprise at least the following events of (1) expiratory breath magnitude $M_{Exp}$>inspiratory breath magnitude $M_{Ins}$; (2) expiratory breath length $L_{Exp}$<inspiratory breath length $L_{Ins}$; and (3) inspiratory phase oscillation in respiratory pressure measurement.

Figure 2:
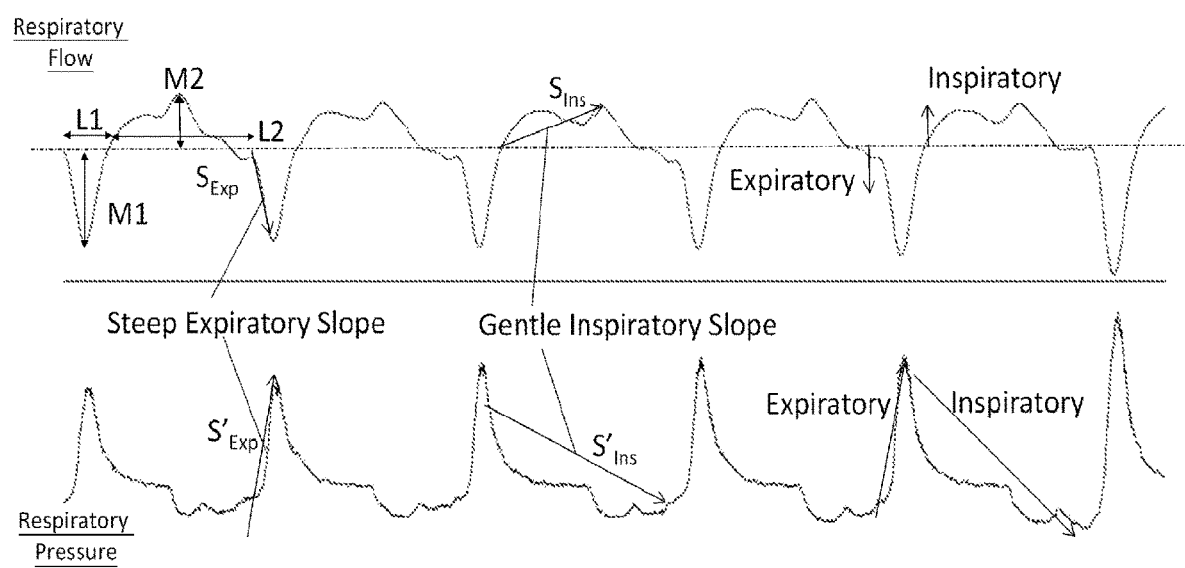
FIG. 2 shows the particularly selected characteristics of inspiratory flow limitation in waveforms related to inspiratory or expiratory slope.

FIG. 2 shows certain particularly selected characteristics of inspiratory flow limitation in waveforms. Based on the exemplary waveforms, the particularly selected characteristics of inspiration flow limitation comprise at least the following events of (1) steep expiratory slope $S_{Exp}$ or $S'_{Exp}$; and (2) gentle inspiratory slope $S_{Ins}$ or $S'_{Ins}$.

Figure 3:
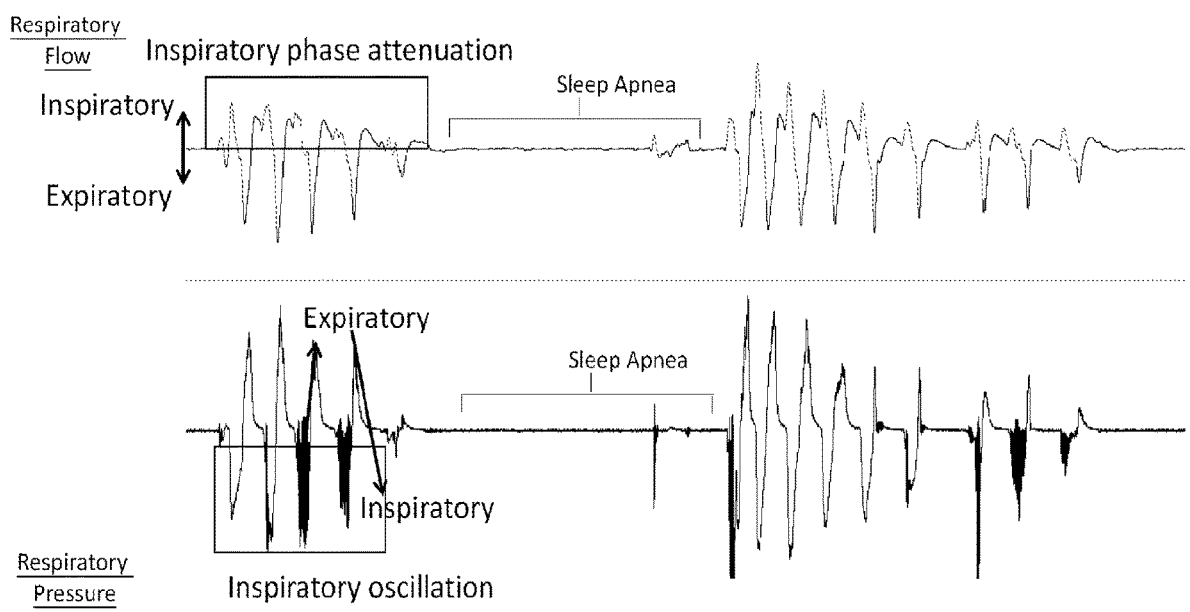
FIG. 3 shows the particularly selected characteristics of inspiratory flow limitation in waveforms related to inspiratory phase attenuation and inspiratory oscillation.

FIG. 3 shows certain particularly selected characteristics of inspiratory flow limitation in waveforms. Based on the exemplary waveforms, the particularly selected inspiratory oscillation in respiratory pressure measurement or inspiratory phase attenuation in respiratory flow measurement as characteristics of inspiration flow limitation is shown. Inspiration flow limitation can be characterized by inspiratory phase attenuation in respiratory flow measurement over several periods of breathing cycles. The magnitude of the inspiratory flow decreases gradually over several breathing cycles. The inspiratory oscillation in the respiratory pressure measurement increases gradually over several breathing cycles as well.

Figure 4:
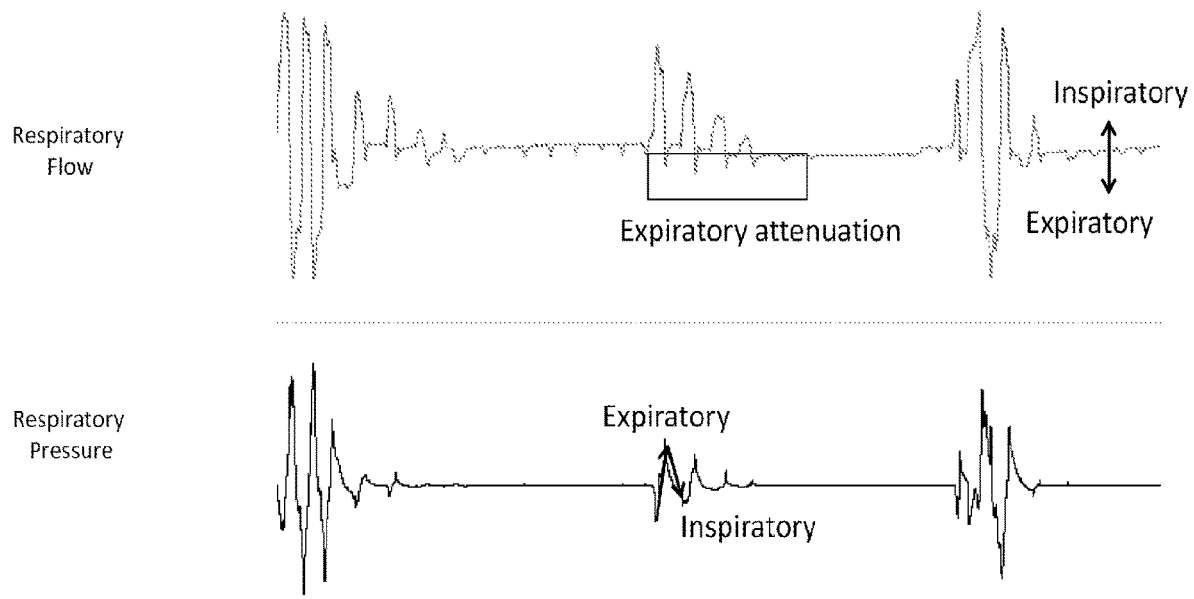
FIG. 4 shows the particularly selected characteristics of expiratory flow limitation in waveforms related to expiratory attenuation.

FIG. 4 provides another example of the particularly selected characteristics of expiratory flow limitation in waveforms where expiratory attenuation is shown. Expiration flow limitation can be characterized by expiratory phase attenuation in respiratory flow measurement over several periods of breathing cycles. Besides, expiratory oscillation in respiratory pressure measurement could be the characteristic of expiratory flow limitation. The magnitude of the expiratory flow decreases over several breathing cycles. The expiratory slope decreases gradually over several breathing cycles as well.

Figure 5:
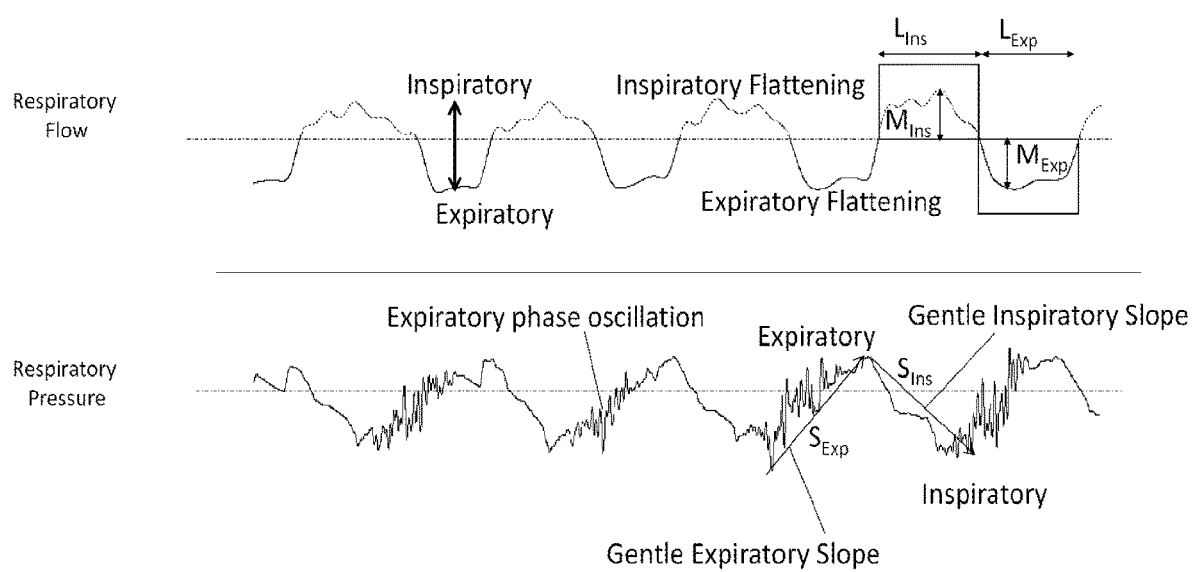
FIG. 5 provides another selected characteristic of mixed flow limitation, where several events of mixed flow limitation in waveforms are shown.
Figure 6:
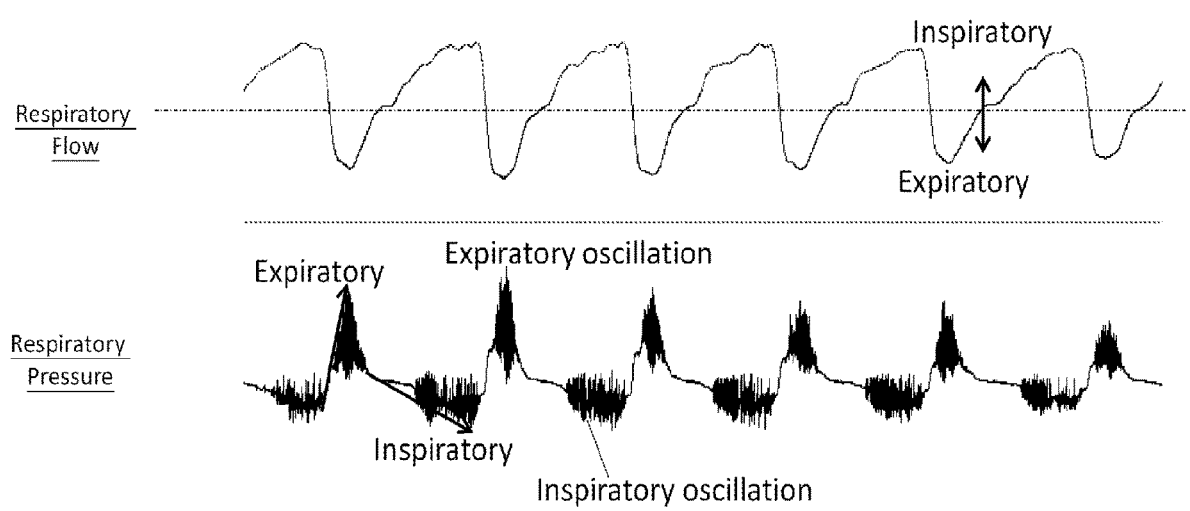
FIG. 6 provides another exemplary event of mixed flow limitation in waveform showing expiratory phase oscillation and/or inspiration phase oscillation in respiratory pressure measurement.

FIG. 5 provides another particularly selected characteristic of mixed flow limitation event, where several events of mixed flow limitation in waveforms are shown. Based on the exemplary waveforms of mixed flow limitation, the particularly selected characteristics of inspiration flow limitation comprises at least the following events of (1) expiratory breath magnitude $M_{Exp}$ similar to inspiratory breath magnitude $M_{Ins}$; (2) expiratory breath length $L_{Exp}$ similar to inspiratory breath length $L_{Ins}$; and (3) gentle expiratory slope $S_{Exp}$ and gentle inspiratory slope $S_{Ins}$. FIG. 6 provides yet another exemplary event of mixed flow limitation in waveform showing the particularly selected expiratory phase oscillation and/or inspiration phase oscillation in respiratory pressure measurement.

Based on the particularly selected air flow and pressure patterns disclosed in FIGS. 1-6, the subjects are characterized in four groups: 1) patients having inspiratory flow limitation patterns, 2) patients having expiratory flow limitation patterns, 3) patients having both inspiratory and expiratory flow limitation patterns; and 4) patients not classified. In some instances, patients have both inspiratory and expiratory flow limitation. In some instances, patients have central/mixed apnea or Cheyne-Stokes respiration that the respiratory effort (chest movement) stops or diminishes.

Cheyne-Stokes respiration is an abnormal pattern of breathing characterized by progressively deeper and sometimes faster breathing, followed by a gradual decrease that results in a temporary stop in breathing called an apnea. The pattern repeats, with each cycle usually taking 30 seconds to 2 minutes. It is an oscillation of ventilation between apnea and hyperpnea with a crescendo-diminuendo pattern, and is associated with changing serum partial pressures of oxygen and carbon dioxide.

The disclosed air flow and pressure patterns in FIGS. 1-6 may be attributed to certain airway tissue compositions or movements. For example, more expiratory flow limitation may be attributed to such that the outward flow tends to lift up the soft palate/nasal valve which blocks the upper airway. On the other hand, the inward flow tends to push down the soft palate/nasal valve and opens the airway. More inspiratory flow limitation is thus may be attributed to the falling tongue. The negative pressure in the lower airway might further pull the tongue to close the airway. Based on the particularly selected characteristics disclosed in the present invention, which may attribute to certain patient conditions, these flow limitation patterns are useful to characterize patients and as bases to choose suitable OSA treatment devices.

Figure 7:
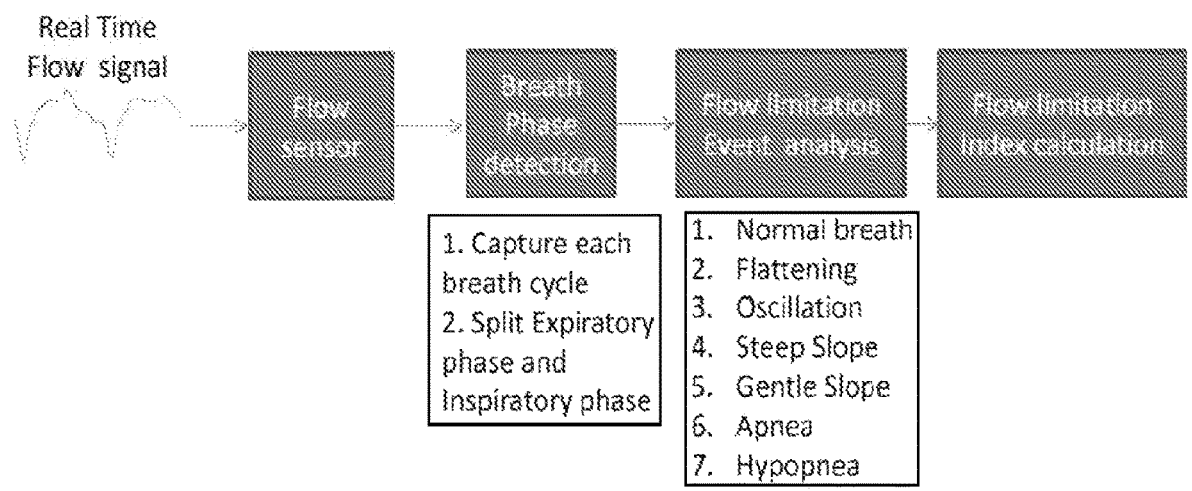
FIG. 7 is a diagram showing a method for characterizing flow limitation pattern.

In some embodiments, a method for characterizing flow limitation pattern is shown in the flow chart of FIG. 7. The real time flow signal is picked up (measured) by a breath flow sensor. In some embodiments, the breath flow sensor is a nasal pressure sensor, an ultrasound flow sensor, a thermistor sensor, a microphone, or other suitable sensors to detect flow signal. Next, each breath cycle is detected and identified from the acquired flow signal and splits to expiratory phase and inspiratory phase. Each breath cycle is then analyzed and classified in the following flow limitation events, normal breath, flattening, oscillation, steep slope, gentle slope, apnea or hypopnea. The flow limitation index is then calculated based on the events.

Figure 8:
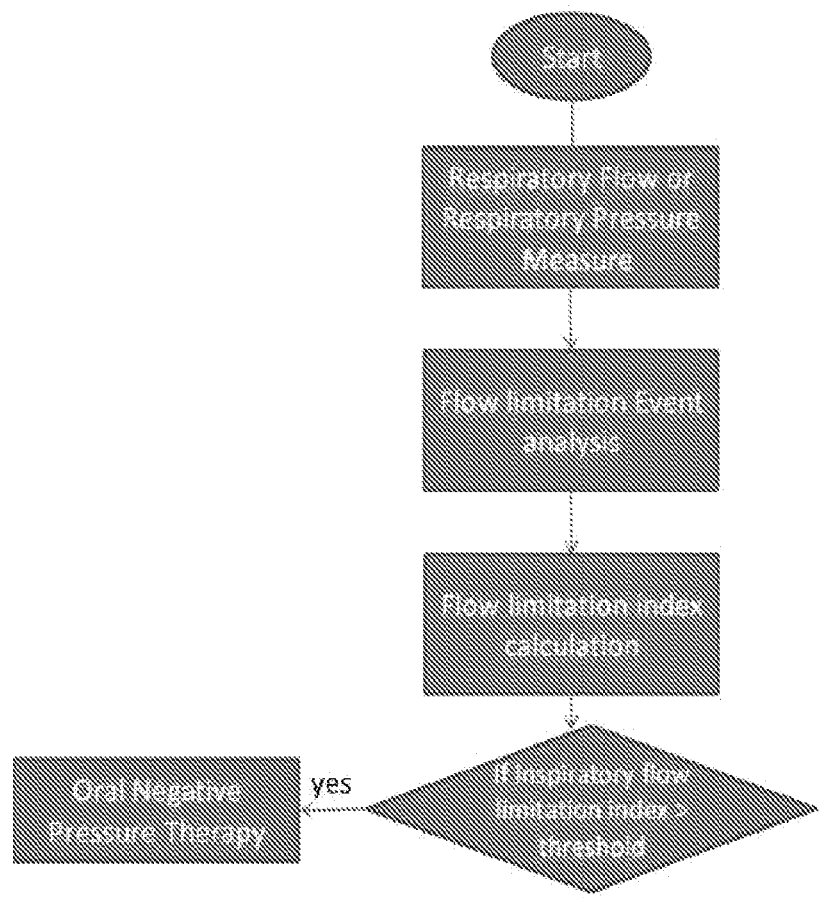
FIG. 8 shows an exemplary flow chart of patient selection suitable for negative pressure therapy.

FIG. 8 shows an exemplary flow chart of patient selection suitable for a negative pressure therapy. The respiratory flow or pressure of a patient is measured. The resulted measurements of flow limitation event are then analyzed based on the following parameters.
Number of total breath cycle: B
Number of inspiratory flow limitation event: IFLE
Number of expiratory flow limitation event: EFLE
Number of mix flow limitation event: MFLE
Based on the measurement, flow limitation indexes are calculated based on the following equations:
Inspiratory flow limitation percentage: IFL=IFLE/B
Expiratory flow limitation percentage: EFL=EFLE/B
Mix flow limitation percentage: MFL=MFLE/B
If the IFL>20% and IFL>EFL, the patients are classified as inspiratory flow limitation group. If the EFL>0.75% and EFL>IFL, the patients are classified as expiratory flow limitation group. If the MFL>1%, the patients are classified as mix flow limitation group. If the patient cannot meet above critters, the patients are not classified. If expiratory flow limitation percentage (a kind of flow limitation indexes) <threshold, the patient is suitable for an oral negative pressure therapy. The threshold is defined as 2%, preferably defined as 1%, and more preferably defined as 0.5%.

Clinical Study of Characteristic of the Polysomnography by Flow Limitation Determination Based on the findings disclosed herein, a clinical study of characteristics of flow limitations was conducted. The results are shown in the table below including previously described flow limitation indexes.

suitable flow sensor, or combination thereof, is applied to a patient, where a controller (comprising a signal processing unit) is connected to the sensor for collection and processing of the sensing signals. The signals are collected and analyzed and the flow limitations are identified. If an inspiratory flow limitation with a particular selected characteristic disclosed herein is detected, a negative pressure source will apply to the patient. If not, a positive pressure source will apply to the patient.

Figure 10:
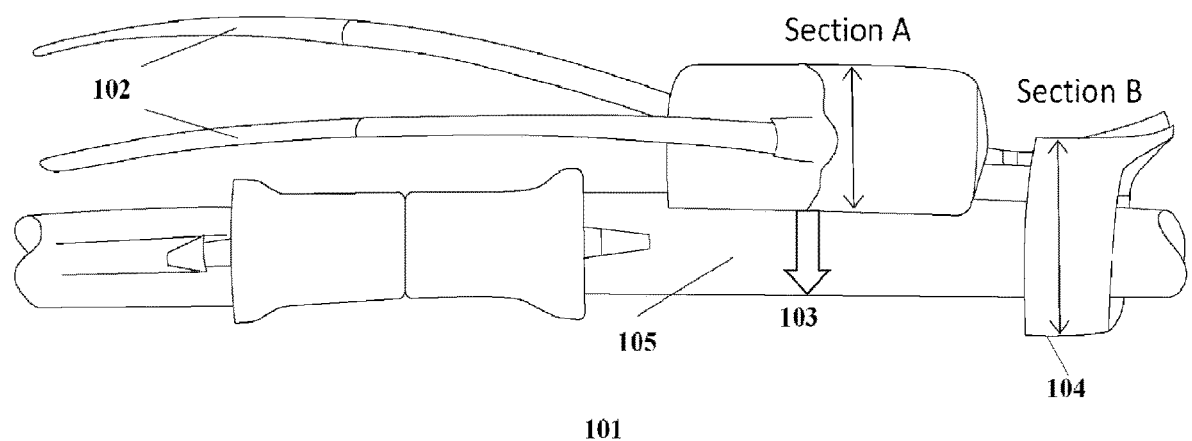
FIG. 10 shows a non-limited exemplary flow limitation detection sensor module 101 applied to patient's oral interface.
Figure 10:
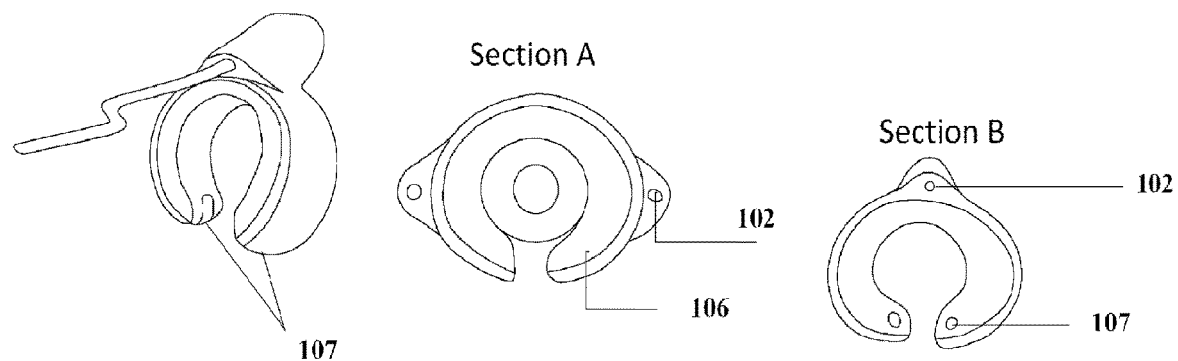

FIG. 10 shows a non-limited exemplary flow limitation detection sensor module 101 applied to patient's nose. The exemplary flow limitation detection sensor module comprises signal wires 102, a signal processing unit 103 clamped on a tube 105, a nose clamp sensor 104. The front view of the nose claim sensor 104 shows where the sensor 107 is located. The cross section of the signal processing unit 103 (Section A) shows a signal wire 102 and soft elastic material 106. The cross section of the nose clamp sensor 104 (Section B) shows the signal wire 102 and where the sensor 107 is located.

Figure 11:
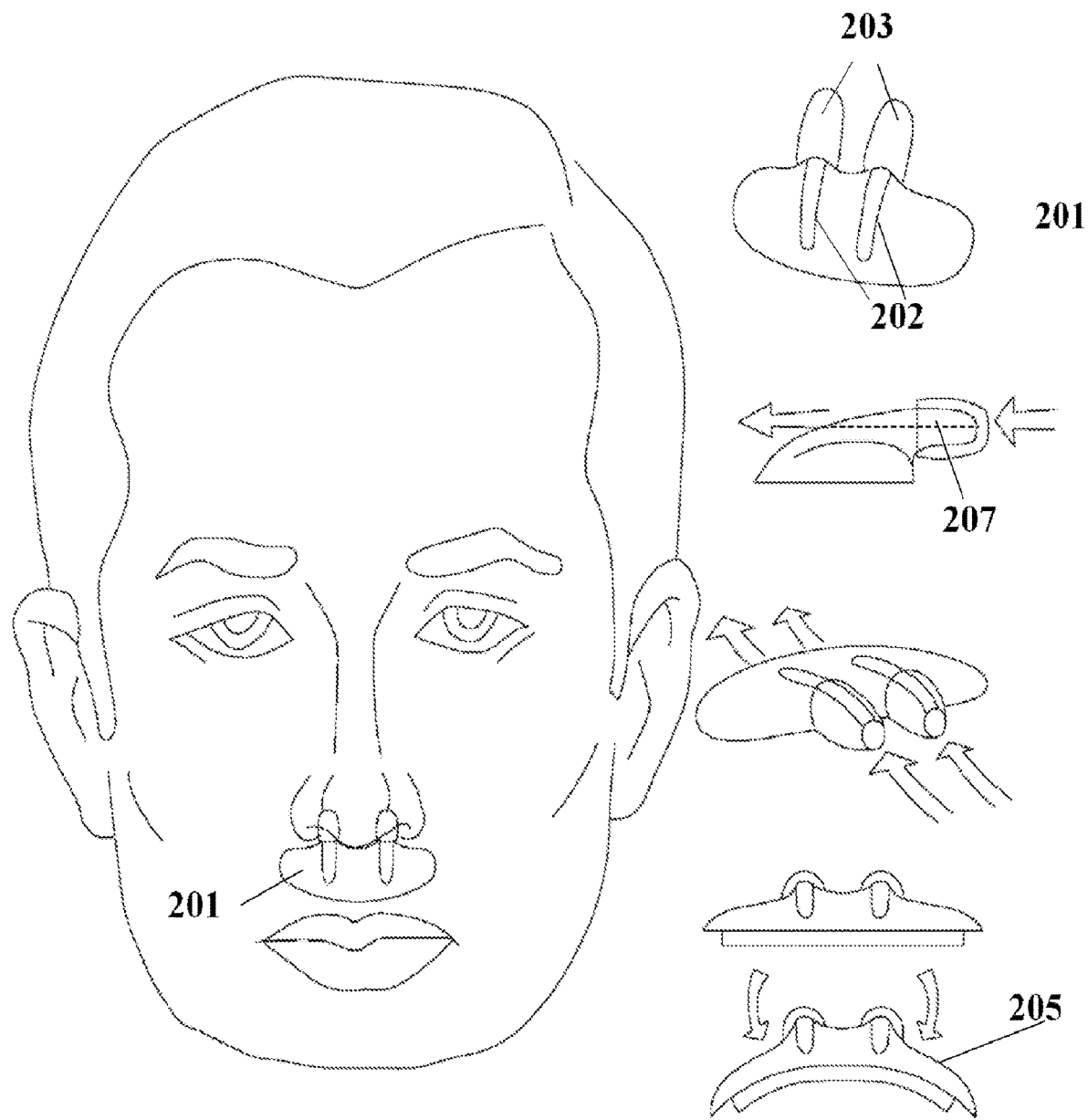
FIG. 11 shows a diagram of how to apply an exemplary flow limitation detection sensor module 201 via nose clamping.

FIG. 11 shows a diagram of how to apply an exemplary flow limitation detection sensor module 201 via nose clamping. A nose clamp 203 is inserted to a patient's nose where two open air channel 202 are shown. A sensor is located at 207 of the air channel 202 where air goes through (breathing in and out). A bendable soft material housing 205 provides a comfortable fit to patient.

Figure 12:
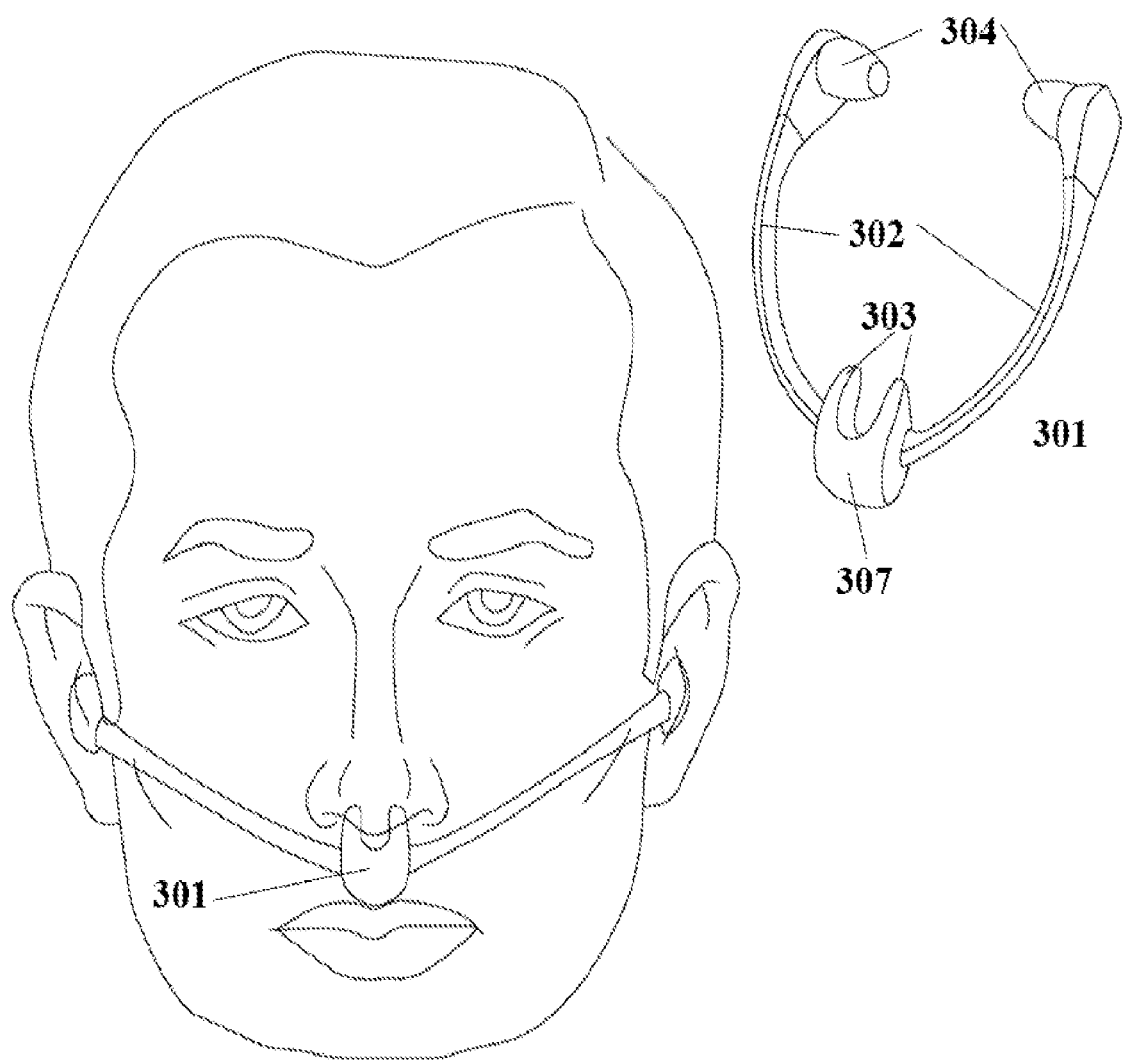
FIG. 12 provides another embodiment of the flow limitation detection sensor module 301 where ear plugs 304 and note clamp 303 are connected via the wires 302.

FIG. 12 provides another embodiment of the flow limitation detection sensor module 301 where ear plugs 304 and nose clamp 303 are connected via the wires 302. A sensor is located at 307.

Figure 13:
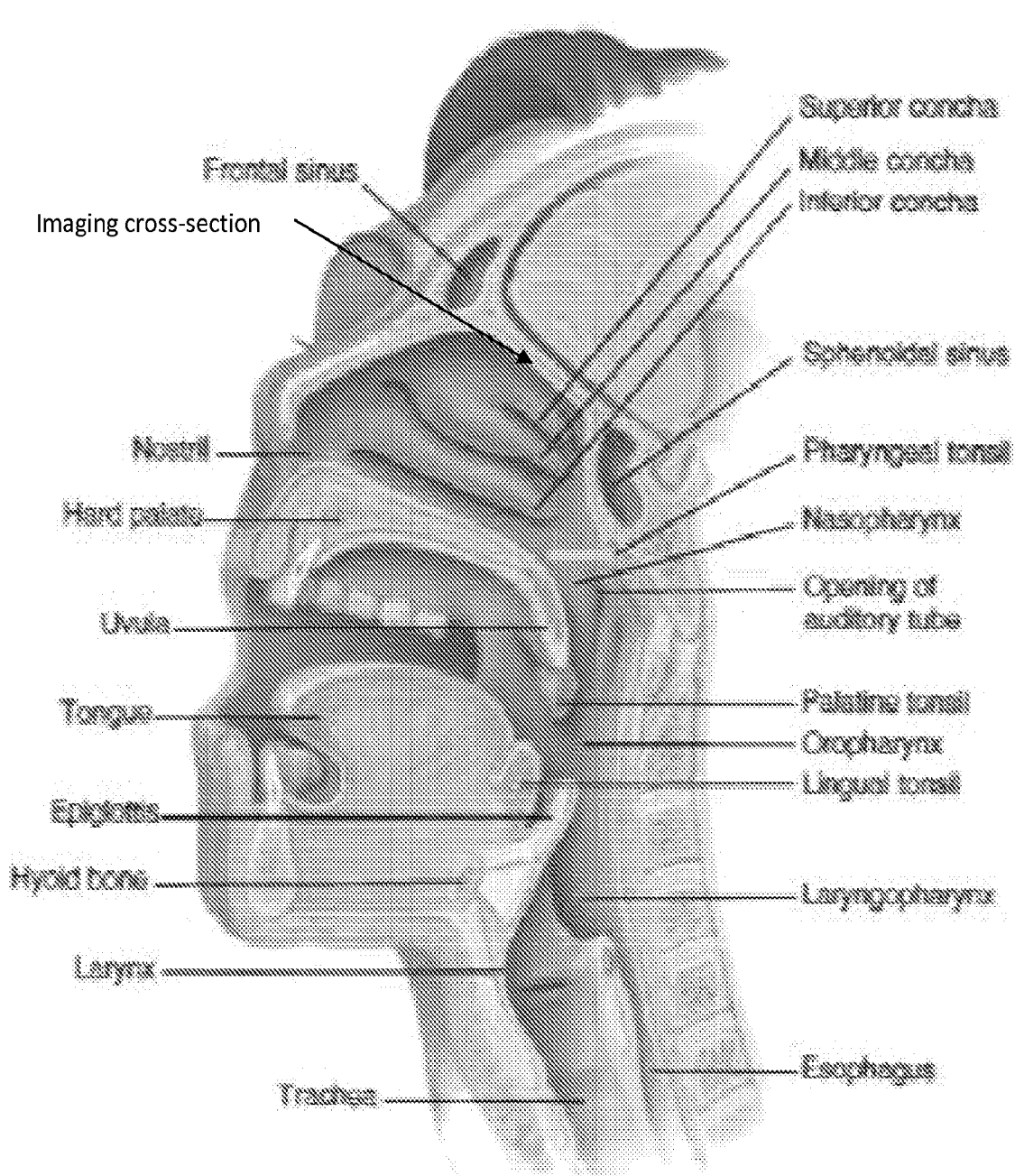
FIG. 13 shows a diagram where an exemplary upper airway endoscopic imaging is taken with Muller Maneuver.

FIG. 13 shows a diagram where an exemplary upper airway endoscopic imaging is taken with Muller Maneuver.

Figure 14:
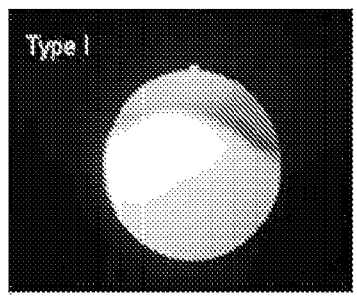
FIG. 14 provides three types of exemplary upper airway endoscopic imaging: Type I: posteroanterior collapse; Type II: lateral collapse; Type III: annular collapse
Figure 14:
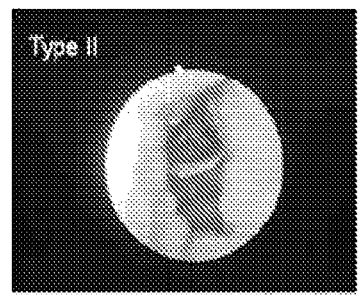
Figure 14:
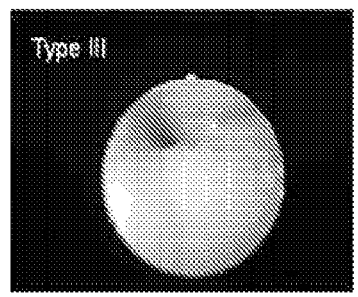
Figure 14:
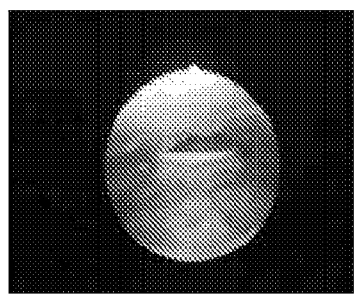
Figure 14:
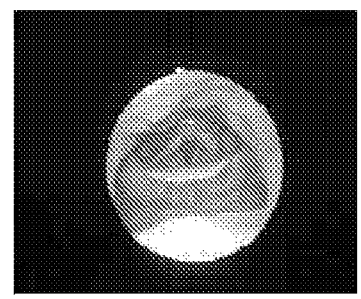
Figure 14:
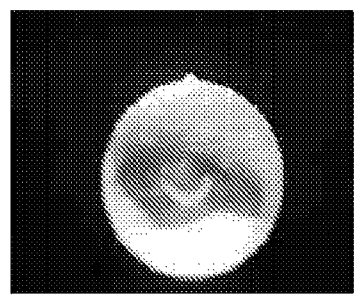
Figure 15:
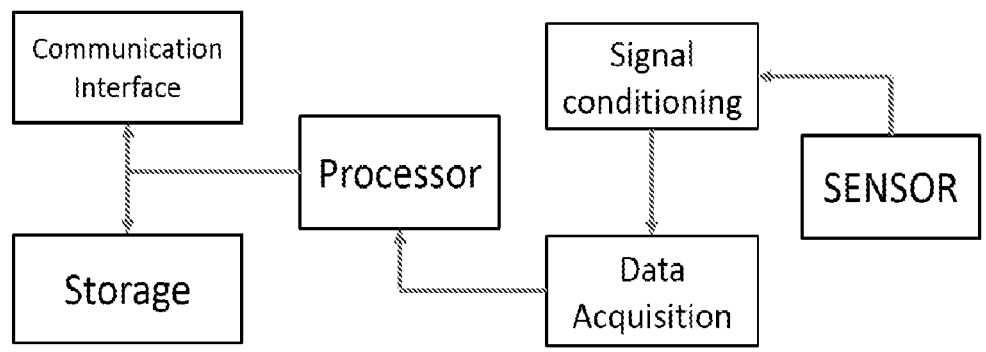
FIG. 15 shows a simplified block diagram of a system for detecting flow limitation of obstructive sleep apnea (OSA) patients.

FIG. 14 provides three types of exemplary upper airway endoscopic imaging: Type I: posteroanterior collapse; Type II: lateral collapse; Type III: annular collapse FIG. 15 shows a simplified block diagram of a system for detecting flow limitation of obstructive sleep apnea (OSA) patients. The system for detecting flow limitation of obstructive sleep apnea (OSA) patient comprising: a sensor unit, for detecting polysomnography of an OSA patient and generating a flow limitation signal; a signal conditioning unit, coupled to the sensor unit, for amplifying the flow limitation

| Patient # | AHI reduction | IFLE | EFLE | MFLE | All Breaths (B) | (EFL + MFL)/ All flow limitation event | EFL |
|---|---|---|---|---|---|---|---|
| 4  | −84.78% | 947  | 42  | 20  | 6410 | 6.14%  | 0.66% |
| 7  | −37.21% | 799  | 132 | 106 | 5934 | 22.95% | 2.22% |
| 8  | −55.71% | 422  | 86  | 283 | 5188 | 46.65% | 1.66% |
| 10 | −9.68%  | 696  | 99  | 178 | 4108 | 28.47% | 2.41% |
| 16 | −47.37% | 1    | 17  | 0   | 4082 | 94.44% | 0.42% |
| 11 | −10.95% | 14   | 39  | 15  | 2040 | 79.41% | 1.91% |
| 25 | −53.03% | 1932 | 20  | 807 | 3344 | 29.97% | 0.60% |
| 3  | −43.67% | 127  | 9   | 14  | 4096 | 15.33% | 0.22% |
| 28 | −52.38% | 814  | 27  | 411 | 3556 | 34.98% | 0.76% |
| 29 | −24.56% | 1894 | 139 | 293 | 5100 | 18.57% | 2.73% |
| 30 | −28.71% | 2238 | 131 | 457 | 5223 | 20.81% | 2.51% |
| 32 | −89.57% | 1299 | 12  | 65  | 4334 | 5.60%  | 0.28% |
| 34 | −63.96% | 145  | 19  | 14  | 4217 | 18.54% | 0.45% |
| 35 | −11.92% | 34   | 2   | 8   | 3788 | 22.73% | 0.05% |

Figure 9:
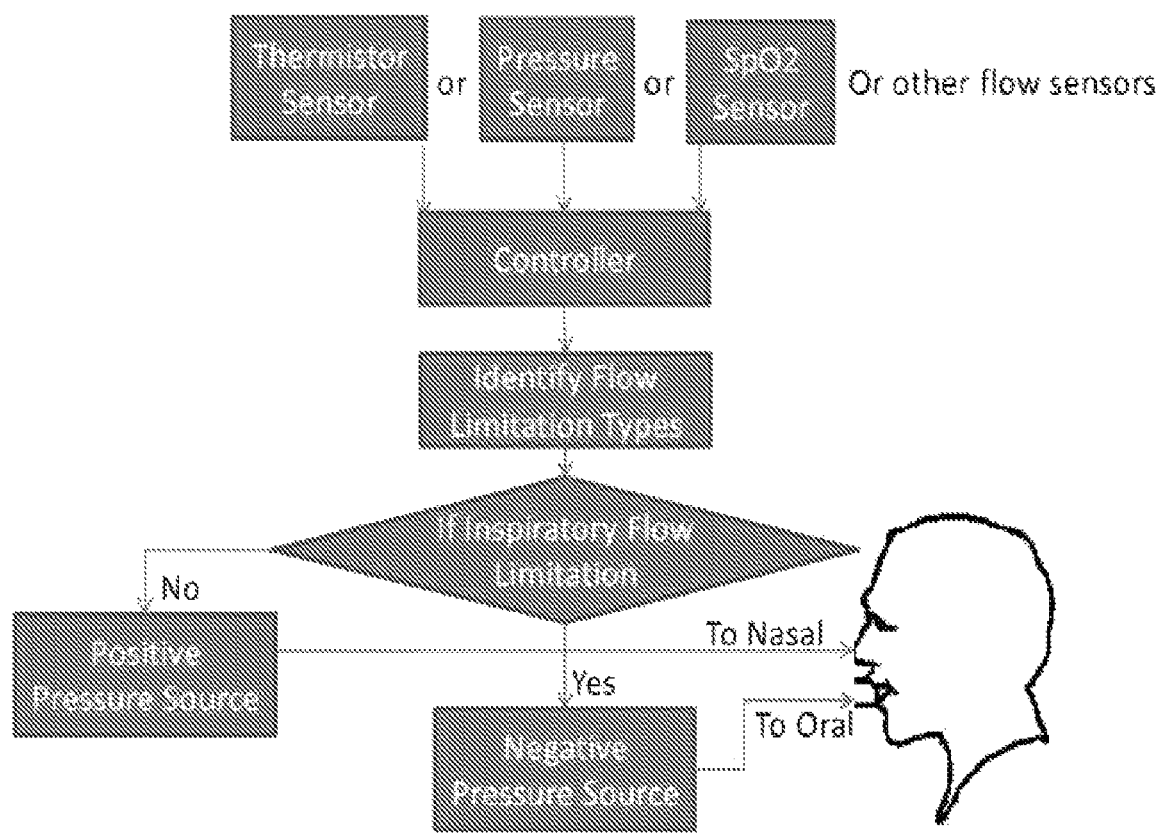
FIG. 9 shows an exemplary flow chart of applying invention method for patient selection of suitable OSA therapy.

FIG. 9 shows an exemplary flow chart of applying invention method for patient selection of suitable OSA therapy. A breath flow sensor such as a thermistor sensor, a pressure sensor, a SpO2 sensor, a pneumotach transducer, or other signal and filtering out unwanted noises; a data acquisition unit, for converting the flow limitation signal to a digital data; a processor unit, for operating the digital data to generate flow limitation indexes; a storage unit for saving the digital data and the flow limitation indexes; and a communication interface unit, for communicating with users and external devices.

Figure 16:
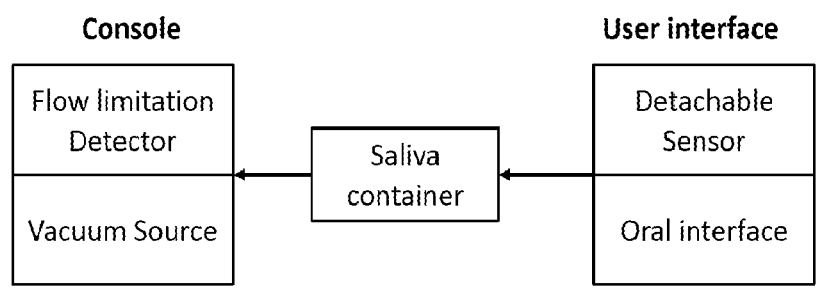
FIG. 16 shows a system for detecting flow limitation of obstructive sleep apnea (OSA) patients combined with negative pressure therapy.

FIG. 16 shows a system for detecting flow limitation of obstructive sleep apnea (OSA) patients combined with negative pressure therapy. The system for detecting flow limitation of obstructive sleep apnea (OSA) patient and combining with negative pressure therapy comprising: a sensor unit, for detecting polysomnography of an OSA patient and generating a flow limitation signal; a signal conditioning unit, coupled to the sensor unit, for amplifying the flow limitation signal and filtering out unwanted noises; a data acquisition unit, for converting the flow limitation signal to a digital data; a processor unit, for operating the digital data to generate flow limitation indexes; a storage unit for saving the digital data and the flow limitation indexes; and a communication interface unit, for communicating with users and external devices; and further comprising: a negative pressure source, for providing a negative pressure to an OSA patient; a tube with two terminals, one terminal connecting the negative pressure source and the other terminal placed in the OSA patient's oral cavity deviling a negative pressure from the negative pressure source to the OSA patient's oral cavity; an oral interface formed on the terminal placed in the OSA patient's cavity, for maintaining sealing of the OSA patient's oral cavity while the negative pressure is being delivered; a saliva container connected to the tubing, for collecting saliva secreted from the OSA patient's oral; a console, for controlling the negative pressure source based on the flow limitation; and a positioner, to place the sensor on the oral interface.

In some embodiments provide a device for use in accordance with practice of the invention methods comprising a flow limitation detection sensor module. In certain embodiments, the flow limitation detection sensor module comprises a nose clamp, and a sensor. In certain embodiments, the sensor is a thermistor sensor, a pressure sensor, a flow sensor, a pneumotach transducer, a SpO2 sensor, or combination thereof. In certain embodiments, the flow limitation detection sensor module further comprises ear plugs connected to the nose clamp. In certain embodiments, the sensor is located where an air is breathing though.

Clinical Study of Patient Selection by Flow Limitation Determination

Based on the findings disclosed herein, a clinical study of patient selection for negative oral pressure therapy by invention selected characteristics of flow limitations was conducted. The results are shown in the table below including four groups of patients with inspiratory flow limitation, with expiratory flow limitation, with both flow limitations, and not classified, respectively. The responder group is defined for those patients having apnea-hypopnea index (AHI) reduction >40%.

| Inspiratory flow limitation | Expiratory flow limitation | Both | Not Classified |
|---|---|---|---|
| IFL #001 (AHI - 37.2%) | EFL #001 (AHI 3%) | MFL #001 (AHI - 0.6%) | NC #001 (AHI - 0.3%) |
| IFL #002 (AHI - 28.7%) | EFL #002 (AHI 0%) | MFL #002 (AHI - 9.7%) | NC #002 (AHI - 13.4%) |
| IFL #003 (AHI - 24.6%) | | MFL #003 (AHI 3%) | |
| IFL #004 (AHI - 43.7%)* | | MFL #004 (AHI - 24.9%) | |
| IFL #005 (AHI - 84.8%)* | | | |
| IFL #006 (AHI - 55.7%)* | | | |
| IFL #007 (AHI - 47.4%)* | | | |
| IFL #008 (AHI - 53.0%)* | | | |
| IFL #009 (AHI - 52.4%)* | | | |
| IFL #010 (AHI - 89.6%)* | | | |

*Responder group (apnea-hypopnea index (AHI) reduction >40%)

In some embodiments provide yet another method for characterizing an OSA patient by taking images of upper airway endoscopic imaging during Muller maneuver and analyzing said images.

FIG. 13 shows a diagram where an exemplary upper airway endoscopic imaging is taken with Muller Maneuver.

FIG. 14 provides three types of exemplary upper airway endoscopic imaging: Type I: posteroanterior collapse; Type II: lateral collapse; Type III: annular collapse Müller Maneuver This technique is designed to look for collapsed sections of airways such as the trachea and upper airways. In this maneuver, the patient attempts to inhale with his mouth closed and his nostrils plugged, which leads to a collapse of the airway. Introducing a flexible fiberoptic scope into the hypopharynx to obtain a view, the examiner may witness the collapse and identify weakened sections of the airway. Müller's maneuver is used to help determine the cause of sleep apnea. A positive test result means the site of upper airway obstruction is likely below the level of the soft palate, and the patient will probably not benefit from an uvulopalatopharyngoplasty alone. This maneuver is very helpful in doing MRI for sleep apnea, when sedation to patient can be avoided.

An exemplary upper airway endoscopic imaging with Muller Maneuver is shown in FIG. 14 taken from patients at the position shown in FIG. 13. FIG. 14 provides three types of imaging: Type I: posteroanterior collapse; Type II: lateral collapse; Type III: annular collapse.

The following study results were collected based on collapse direction. Screen Criteria: Collapse Direction

| Collapse Directions | Responder | Non-Responder | All | Responder % |
|---|---|---|---|---|
| All | 9 | 9 | 18 | 50.0% |
| Posteroanterior (Type I) | 6 | 1* | 7 | 85.7% |
| Lateral (Type II) | 2 | 2 | 4 | 50.0% |
| Annular(Type III) | 1 | 6 | 7 | 14.2% |

*Type I failed case is due to central apnea which is not related to airway obstruction AHI = 57.4, Apnea: 32, Central + Mix = 23, Hypopnea = 2.4

The study showed that OSA patient response rate is at the highest for posteroanterior collapse during Muller Maneuver.

In some embodiments provide methods for characterizing obstructive sleep apnea (OSA) patients for use in the treatment of OSA comprising taking images of upper airway endoscopic imaging with Muller maneuver, analyzing said images, and characterizing said OSA patients based on a characteristic of the images. In certain embodiments, the characteristic of the images is posteroanterior, lateral, or annular collapse. In certain embodiments, posteroanterior collapse is used for characterizing obstructive sleep apnea (OSA) patients.

In some embodiments provide methods selecting OSA patient for a suitable OSA treatment comprising taking images of upper airway endoscopic imaging with Muller maneuver; analyzing said images; and selecting the suitable OSA treatment based on a characteristic of the images. In certain embodiments, the characteristic of the images is posteroanterior, lateral, or annular collapse. In certain embodiments, posteroanterior collapse is used as the characteristic for OSA patient selection.

FIG. 15 shows a simplified block diagram of a system for detecting flow limitation of obstructive sleep apnea (OSA) patients. The system for detecting flow limitation of obstructive sleep apnea (OSA) patient comprising: a sensor unit, for detecting polysomnography of an OSA patient and generating a flow limitation signal; a signal conditioning unit, coupled to the sensor unit, for amplifying the flow limitation signal and filtering out unwanted noises; a data acquisition unit, for converting the flow limitation signal to a digital data; a processor unit, for operating the digital data to generate flow limitation indexes; a storage unit for saving the digital data and the flow limitation indexes; and a communication interface unit, for communicating with users and external devices.

FIG. 16 shows a system for detecting flow limitation of obstructive sleep apnea (OSA) patients combined with negative pressure therapy. The system for detecting flow limitation of obstructive sleep apnea (OSA) patient and combining with negative pressure therapy comprising: a sensor unit, for detecting polysomnography of an OSA patient and generating a flow limitation signal; a signal conditioning unit, coupled to the sensor unit, for amplifying the flow limitation signal and filtering out unwanted noises; a data acquisition unit, for converting the flow limitation signal to a digital data; a processor unit, for operating the digital data to generate flow limitation indexes; a storage unit for saving the digital data and the flow limitation indexes; and a communication interface unit, for communicating with users and external devices; and further comprising: a negative pressure source, for providing a negative pressure to an OSA patient; a tube with two terminals, one terminal connecting the negative pressure source and the other terminal placed in the OSA patient's oral cavity deviling a negative pressure from the negative pressure source to the OSA patient's oral cavity; an oral interface formed on the terminal placed in the OSA patient's cavity, for maintaining sealing of the OSA patient's oral cavity while the negative pressure is being delivered; a saliva container connected to the tubing, for collecting saliva secreted from the OSA patient's oral; a console, for controlling the negative pressure source based on the flow limitation; and a positioner, to place the sensor on the oral interface.

In some embodiments provide a device for use in accordance with practice of the invention methods comprising a flow limitation detection sensor module. In certain embodiments, the flow limitation detection sensor module comprises a nose clamp, and a sensor. In certain embodiments, the sensor is a thermistor sensor, a pressure sensor, a flow sensor, a pneumotach transducer, a SpO2 sensor, or combination thereof. In certain embodiments, the flow limitation detection sensor module further comprises ear plugs connected to the nose clamp. In certain embodiments, the sensor is located where an air is breathing though.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating an obstructive sleep apnea (OSA) patient using negative pressure treatment, wherein the negative pressure treatment includes delivering negative pressure to a patient's oral cavity, the method comprising:
   conducting polysomnography testing of said OSA patient comprising obtaining polysomnography (PSG) data of said OSA patient during sleep;
   analyzing, using a processor, the PSG data to classify said OSA patient as one of a plurality of predetermined flow limitations types, wherein the plurality of predetermined flow limitation types comprises Inspiratory Flow Limitation (IFL) type, Expiratory Flow Limitation (EFL) type, Mix Flow Limitation (MFL) type, and Not Classified (NC) type;
   determining if said OSA patient is suitable for said negative pressure treatment based on the predetermined flow limitation type in which the OSA patient was classified; and
   activating, using the processor, a negative pressure source to provide said negative pressure to the oral cavity of the patient if the processor unit determines OSA patient is suitable for the negative pressure treatment.

2. The method of claim 1, wherein said conducting polysomnography testing comprises obtaining inspiratory and expiratory air flow data.

3. The method of claim 2, wherein said analyzing, using a processor, the PSG data comprises analyzing the inspiratory and expiratory air flow data to determine a respective number of one or more inspiratory and expiratory flow limitation events.

4. The method of claim 3, wherein said analyzing the inspiratory and expiratory air flow data comprises analyzing inspiratory and expiratory flow magnitude.

5. The method of claim 3, wherein said analyzing the inspiratory and expiratory air flow data comprises analyzing inspiratory and expiratory flow period length changes.

6. The method of claim 3, wherein said analyzing the inspiratory and expiratory air flow data comprises analyzing inspiratory phase attenuation and expiratory phase attenuation.

7. The method of claim 3, wherein said analyzing the inspiratory and expiratory air flow data comprises analyzing inspiratory and expiratory slope changes.

8. The method of claim 3, wherein said analyzing the inspiratory and expiratory air flow data comprises analyzing inspiratory and expiratory phase oscillations.

9. The method of claim 1, wherein said analyzing, using a processor, the PSG data comprises:
   calculating an Inspiratory Flow Limitation (IFL) percentage and an Expiratory Flow Limitation (EFL) percentage, wherein the IFL percentage is the number of determined inspiratory flow limitation events divided by a number of total breath cycles and the EFL percentage is the number of determined expiratory flow limitation events divided by a number of total breath cycles;

comparing the calculated IFL percentage to one or more predetermined criteria to determine if the OSA patient is the IFL type; and comparing the calculated EFL percentage to one or more predetermined criteria to determine if the OSA patient is the EFL type.

10. The method of claim 1, wherein said comparing the calculated IFL percentage comprises:
   determining if the IFL percentage is greater than 20% and greater than EFL percentage; and
   classifying said OSA patient as the IFL type if the IFL percentage is greater than 20% and greater than the EFL percentage.

11. The method of claim 10, wherein said determining if said negative pressure treatment is suitable comprises:
   determining said negative pressure treatment is suitable for treating said OSA patient if said OSA patient is classified as the IFL type.

12. The method of claim 1, wherein said comparing the EFL percentage comprises:
   determining if the EFL percentage is greater than 0.75% and greater than the IFL percentage; and
   classifying said OSA patient as the EFL type if the EFL percentage is greater than 0.75% and greater than the IFL percentage.

13. The method of claim 12, wherein said determining if said negative pressure treatment is suitable comprises:
   determining said negative pressure treatment is suitable for treating said OSA patient if said OSA patient is classified as the EFL type and the EFL percentage is less than a predetermined threshold.

14. The method of claim 13, wherein the predetermined threshold is defined as 2%.

15. The method of claim 13, wherein the predetermined threshold EFL percentage is 1%.

16. The method of claim 13, wherein the predetermined threshold EFL percentage is 0.5%.

17. The method of claim 1, wherein said analyzing, using a processor, the PSG data further comprises:
   analyzing the inspiratory and expiratory air flow data to determine a number of mixed flow limitation events;
   calculating a Mixed Flow Limitation (MFL) percentage, wherein the MFL percentage is the number of determined mixed flow limitation events divided by a number of total breath cycles;
   determining if the MFL percentage is greater than 1%; and
   classifying said OSA patient as the MFL type if the MFL percentage is greater than 1%.

18. The method of claim 17, wherein the OSA patient is classified as the NC type if the OSA patient is not classified as any one of the IFL type, the EFL type and the MFL type.

19. A system for treating an obstructive sleep apnea (OSA) patient using a negative pressure treatment, wherein the negative pressure treatment includes delivering negative pressure to a patient's oral cavity, the system comprising:
   a sensor unit, for detecting inspiratory and expiratory air flow of said OSA patient and generating inspiratory and expiratory flow limitation signals;
   a signal conditioning unit, coupled to the sensor unit, for amplifying the inspiratory and expiratory flow limitation signals and filtering out unwanted noises;
   a data acquisition unit, for converting the inspiratory and expiratory flow limitation signals to a digital data, wherein the digital data comprises inspiratory and expiratory air flow data;
   a processor unit, coupled to the data acquisition unit, configured to:
      analyze the PSG data to classify said OSA patient as one of a plurality of predetermined flow limitation types, wherein the plurality of predetermined flow limitation types comprises Inspiratory Flow Limitation (IFL) type, Expiratory Flow Limitation (EFL) type, Mix Flow Limitation (MFL) type, and Not Classified (NC) type; and
      determine if said OSA patient is suitable for said negative pressure treatment based on the predetermined flow limitation type in which the OSA patient was classified;
   wherein the processor unit is configured to couple to a negative pressure source and to activate the negative pressure source to provide the negative pressure to the oral cavity of the patient if the processor unit determines said negative pressure treatment is suitable for treating said OSA patient.

20. A system of claim 19, further comprising:
   the negative pressure source, for providing the negative pressure to the oral cavity of the OSA patient; and
   a tube for delivering negative pressure from the negative pressure source to the OSA patient's oral cavity.

21. The system of claim 19, wherein the sensor unit is a thermistor sensor, a pressure sensor, a flow sensor, a pneumotach transducer, a SpO2 sensor, a microphone, or combination thereof.

22. The system of claim 19, wherein the sensor unit further comprises a nose clamp.

23. The system of claim 22, wherein the sensor unit further comprises ear plugs connected to the nose clamp.

24. The method of claim 1, further comprising:
   taking endoscopic images of upper airway with Muller maneuver;
   analyzing said images;
   classifying said OSA patient as a posteroanterior type, a lateral type or an annular collapse type based on the analysis of the images; and
   determining said OSA patient is suitable for negative pressure treatment if said OSA patient is classified as the posteroanterior type.

* * * * *